(12) United States Patent
Wick et al.

(10) Patent No.: US 9,157,917 B2
(45) Date of Patent: *Oct. 13, 2015

(54) APPLICATIONS OF INDOLOINDOLE AND INDOLOQUINOLINE DYES

(75) Inventors: Lukas Wick, Winterthur (CH); Urs Spitz, Herrliberg (CH); Christophe Weymuth, Zürich (CH); Günter Schabert, Goldach (CH); Thomas Mayer, Bodman-Ludwigshafen (DE); Alexander Bayer, Goldach (CH)

(73) Assignee: Biosynth AG (CH)

( * ) Notice: Subject to any disclaimer, the term of this patent is extended or adjusted under 35 U.S.C. 154(b) by 104 days.

This patent is subject to a terminal disclaimer.

(21) Appl. No.: 13/883,067

(22) PCT Filed: Nov. 4, 2011

(86) PCT No.: PCT/EP2011/069423
§ 371 (c)(1),
(2), (4) Date: Jul. 11, 2013

(87) PCT Pub. No.: WO2012/059583
PCT Pub. Date: May 10, 2012

(65) Prior Publication Data
US 2014/0377783 A1    Dec. 25, 2014

(30) Foreign Application Priority Data

Nov. 4, 2010 (EP) .................... 10190047

(51) Int. Cl.
| | | |
|---|---|---|
| *C07D 221/18* | (2006.01) |
| *C09B 67/08* | (2006.01) |
| *G01N 33/58* | (2006.01) |
| *C09B 57/00* | (2006.01) |
| *C09B 67/44* | (2006.01) |
| *C12Q 1/04* | (2006.01) |
| *C12Q 1/10* | (2006.01) |
| *C12Q 1/34* | (2006.01) |
| *C12Q 1/44* | (2006.01) |

(52) U.S. Cl.
CPC .............. *G01N 33/583* (2013.01); *C09B 57/00* (2013.01); *C09B 67/0083* (2013.01); *C12Q 1/04* (2013.01); *C12Q 1/10* (2013.01); *C12Q 1/34* (2013.01); *C12Q 1/44* (2013.01); *G01N 2333/938* (2013.01)

(58) Field of Classification Search
USPC .......................... 546/73; 548/426; 8/568, 574
See application file for complete search history.

(56) References Cited

FOREIGN PATENT DOCUMENTS

| | | |
|---|---|---|
| EP | 0 641 351 B1 | 10/1996 |
| WO | WO 98/38332 | 9/1998 |
| WO | WO 2010/128120 A1 | 11/2010 |

OTHER PUBLICATIONS

Crawford, L.A., Clemence, N.C., McNab, H., and Tyas, R.G., 2008, Isoindolo[2,1-a] indol-6-one—a new pyrolytic synthesis and some unexpected chemical properties, Organic & Biomolecular Chemistry, p. 2334-2339.

Lee, H.S., Kim, S.H., Kim, Y.M and Kim, J.N., 2010, An expedient synthesis of indolo [1,2-a] quinolines via Mn(OAc)3-mediated oxidative free radical cyclization and NaI/O2-assisted dealkoxycarbonylation/aerobic oxidation cascade, Tetrahedron Letters 51, p. 5071-5075.

*Primary Examiner* — Charanjit Aulakh
(74) *Attorney, Agent, or Firm* — George Pappas (57) ABSTRACT

A novel type of dye systems comprises a selection of 10H-indolo[1,2-a]indole compounds (henceforth abbreviated as IO compounds) and (5H,7H)-indolo[1,2-a]quinoline compounds (henceforth abbreviated as IQ compounds) showing a solvatochromic effect and exhibiting strong fluorescence in a variety of materials such as polypropylene, polyethylene, oils, various solvents, emulsions. Also disclosed are various methods how the IO/IQ compounds can be administered, especially how they can be produced and administered in situ from a precursor, responding to external stimuli such as enzyme activity, temperature and so forth. The response of a precursor to external stimuli can also be used to determine the presence or absence of such stimuli.

33 Claims, 2 Drawing Sheets

APPLICATIONS OF INDOLOINDOLE AND INDOLOQUINOLINE DYES

This application claims priority from PCT application No. PCT/EP2011/069423 filed Nov. 4, 2011 which claims priory from European application No. EP10190047.0 filed on Nov. 4, 2010, the disclosures of which are incorporated herein by reference.

FIELD OF THE INVENTION

The present invention discloses novel applications for 10H-indolo[1,2-a]indole compounds (henceforth abbreviated as IO compounds) and (5H,7H)-indolo[1,2-a]quinoline compounds (henceforth abbreviated as IQ compounds), based on the discovery that IO/IQ compounds show a solvatochromic effect and can exhibit strong fluorescence in a variety of materials such as polypropylene, polyethylene, oils, various solvents, emulsions etc. The invention also discloses various methods how the IO/IQ compounds can be administered, especially how they can be produced and administered in situ from a precursor, responding to external stimuli such as enzyme activity, temperature and so forth. The response of a precursor to external stimuli can also be used to determine the presence or absence of such stimuli.

BACKGROUND OF THE INVENTION

Dyes are compounds used to add color or fluorescence to any kind of material or matrix, e.g. textiles, paper, plastics, biological molecules, cellular structures and so forth. To be suitable for a given application a dye not only needs to have certain chromophoric properties but has also to interact with the matrix in a certain manner. One example is the hematoxylin-eosin stain in histology. This staining method takes advantage of the different staining properties of hematoxylin and eosin towards cellular structures. Hematoxylin stains mainly the cell nuclei blue, whereas eosin stains mainly the cytoplasmic proteins red.

Another important property of dyes is that feasible methods must be present to apply the dye to the matrix. An example is the application of vat dyes to fabrics. Vat dyes are a class of water insoluble dyes that can be made soluble by chemical reduction. Fabric is then immersed in a solution of the reduced form, which is then oxidized in the fabric back to the insoluble dye. Thanks to this application method vat dyes are very color fast. The reduced form of a vat dye is a dye precursor that is transformed into the dye upon a given stimulus at a desired location. In such a case the type of stimulus is not of primary concern as long as it does not have any negative side effects on the dyeing process. However, the formation of the dye from the dye precursor through an external stimulus can also be used to specifically detect said external stimulus. In this case a dye precursor functions as an indicator and the type of stimulus transforming the dye precursor into the dye is of primary interest. We will use the term dye precursor as a general term and the term dye indicator for all kinds of dye precursors when the detection of the said stimulus is of primary interest. Transformation of the precursor typically involves the chemical removal or modification of a labile group ("LG") of the precursor in a process mediated by the experience of said stimulus. Such stimuli typically include temperature, light (photo-labile or photochromic indicators), electric field (electrochromic indicators), pressure (piezoelectric indicators), ion concentration (e.g. pH indicators) and biochemical reactivity (e.g. enzyme indicators).

Fluorogenic enzyme indicators based on resorufin, fluorescein or umbelliferone derivatives are well known in the art. Although umbelliferone indicators are most widely used, they show various disadvantages. For example, umbelliferones are blue fluorescent under UV light. This is often undesirable because most media exhibit themselves a natural blue fluorescent background. Accordingly, an emission shifted to green, yellow or red would offer an advantage over umbelliferone indicators.

Because umbelliferone (pKa 7.8) only shows significant fluorescence in the deprotonated state, reading of assays only works satisfactorily at alkaline pH, thus limiting the use of these indicators.

Moreover, some indicators, especially ester type indicators (e.g. acetate, nonanoate, inositol phosphate) of umbelliferone and also fluorescein and resorufin are not very stable in aqueous solutions, so that most assays have to be carried out in a relatively short time frame. More stable indicators would also allow performing assays that need longer incubation times, such as enrichment broths. Also, in certain media fluorescence detection might be difficult due to turbid or quenching components in the media. A method for separating the signal from the interfering media would clearly improve the use of such assays.

WO 2010/128120, which was published on 11 Nov. 2010, i.e. after the priority date claimed by the present application, discloses 10H-Indolo[1,2-a]indole staining of bacterial colonies, e.g. in Agar, but not in a low-polarity host with a room-temperature dielectric constant $\in \leq 10.0$.

The publication by Crawford L. A. et al., "Isoindolo[2,1-a]indol-6-one—a new pyrolytic synthesis and some unexpected chemical properties", Organic & Biomolecular Chemistry, Royal Society of Chemistry, GB, Vol 6, (2008 Jan. 1), pp. 2334-2339, discloses another class of compound, namely iso-indoloindoles. Merely Compound 13 is an indoloindole, but it was only detected as minor product or impurity, and no indications whatsoever are given about its color properties or suitability as a dye.

SUMMARY OF THE INVENTION

Applicants have found types of novel chromogenic and fluorogenic indicators (so called Indoloindole (IO) and Indoloquinoline (IQ) indicators) that respond to certain external stimuli. In the present context, the term external stimulus shall be understood as comprising but not being limited to: temperature variations, electric fields, electromagnetic irradiation, pressure, particular chemical environments such as acidic, alkaline, oxidizing or reducing, presence of enzymes or particular chemical species such as ions, oxygen or oxidizing agents, hydrogen or reducing agents.

Under such a stimulus, said IO/IQ indicators (IO/IQ precursors) are converted through an intramolecular aldol type condensation to corresponding 10H-indolo[1,2-a]indole (IO) and (5H,7H)-indolo[1,2-a]quinoline (IQ) compounds, respectively. These 10H-indolo[1,2-a]indoles and (5H,7H)-indolo[1,2-a]quinoline will generally be designated as IO dyes and IQ dyes, respectively, i.e. their formation goes along with the emergence of a detectable change in color or fluorescence. The present invention discloses novel properties and applications of IO/IQ dyes and IO/IQ precursors.

In particular, the use of IOs and IQs as fluorescent dyes in certain hosts or matrices is disclosed.

Accordingly, one aspect of the invention relates to the use of a 10H-indolo[1,2-a]indole (IO) compound having the general formula (Ia):

or of a (5H,7H)-indolo[1,2-a]quinoline (IQ) compound having the general formula (IIa):

wherein
X is O, NH or S
R1, R2, R3, R4, R5, R6, R7, R8, R9, R10 and R11 are independently selected from the group consisting of hydrogen; C1-4 alkyl; C1-4 alkoxy; fused or linearly connected aryl; fused or linearly connected heteroaryl; halogen; cyano; nitro; formyl; and optionally substituted amino, carboxy, carbonyl, hydroxyl and sulfonyl, as a dye in a low-polarity host.

It shall be pointed out that the terms "aryl" and "heteroaryl" shall not be limited to 6-ring systems and thus shall also include other aromatic or heteroaromatic ring systems, which may optionally be substituted. In particular, they shall also comprise, without limitation, substituents like R12, R13 and R14 as defined further below.

According to another aspect of the invention, there is provided a dye system comprising a compound having the general formula (Ia) or (Ib) dissolved in a low-polarity host.

According to a further aspect of the invention, a method of producing a dye system as defined above comprises the step of providing a precursor compound having the general formula (IIa):

or (IIb):

wherein
R1, R2, R3, R4, R5, R6, R7, R8, R9, R10 and R11 are selected from the group consisting of hydrogen; C1-4 alkyl; C1-4 alkoxy; fused or linearly connected aryl; fused or linearly connected heteroaryl; halogen; cyano; nitro; formyl and optionally substituted amino, carboxy, carbonyl, hydroxy and sulphonyl;
X is selected from O, NH or S;
LG is a labile group with the X-LG moiety being susceptible to conversion by action of an external stimulus; and
Z is selected from O, NH or S;
followed by the step of subjecting said precursor compound to said external stimulus so as to transform said compound of formula (IIa or IIb) to a corresponding compound of formula (Ia or Ib).

IO/IQ dyes can be seen to consist of three modifiable modules A, B, and C as exemplified in the following formula (example of an IO dye where R9=module C):

Each module can contain a broad variety of donor or acceptor substituents X, Y, and Z, resulting in a myriad of possible molecules with different characteristics. Properties such as solubility, binding affinity to certain hosts, color and so forth can be tuned through these modules depending on the desired application.

In the present context, the term "host" will be used in its broadest sense as an environment in or on which the dye of interest is present as a guest. Accordingly, the term "host" will not be limited to solids and will also include certain liquids. Some hosts, especially hydrophobic ones, can increase the fluorescence of IOs/IQs considerably and therefore improve existing methods or enable completely new applications for fluorescent staining in various fields. IO/IQ dyes can show strong fluorescence in certain hosts such as polypropylene (PP) and polyethylene (PE), oil, various solvents, particularly aprotic solvents, emulsions, on a variety of membranes etc.

The term "low polarity host" as used herein will be used to refer to any material with a room-temperature dielectric constant $\epsilon \leq 10.0$.

Hereinabove and in the following, the term "optionally substituted" stands for substitution with a general inert moiety, wherein the term "generally inert" refers herein to any moieties that do not generally interfere with the procedural practices of this invention. Representative examples of generally inert groups or moieties may generally include hydrogen and such organic groups as, for instance, aromatics to include phenyl, alkyl- and/or halogen-substituted phenyl, naphthyl, phenyl-, alkyl and/or halogen-substituted naphthyl; saturated organic residues to include linear and branched alkyl, for example, methyl, ethyl, propyl to include cyclopropyl, butyl to include cyclobutyl and methyl-substituted cyclopropyl, pentyl to include, e.g., cyclopentyl and methyl-substituted cyclobutyl, hexyl to include, e.g., cyclohexyl, methyl-substituted cyclopentyl and dimethyl or ethyl-substituted cyclobutyl, heptyl to include cycloheptyl, etc., octyl to include cyclooctyl, etc.; halogen-substituted alkyl to include halogen-substituted cycloalkyl, e.g., fluoroalkyl, perfluoroalkyl, e.g., trifluoromethyl, and chloralkyl; alkoxy, e.g., methoxy, aromatic-oxy, e.g., phenoxy; alkylthioxy, e.g., methylthioxy; aromatic-thioxy, e.g., phenylthioxy; acyl, e.g., benzoyl and acetyl, and so forth and the like.

The application of IO/IQ dyes to these hosts can be achieved by two methods, namely a direct application of the dye onto or into the matrix and a stimulus dependent application. In a direct application, the dye can, for example, be printed from a solution or suspension onto a solid host or matrix. In an indirect application method the IO/IQ dye is produced in situ from a non-fluorescent IO/IQ precursor (IO/IQ indicator). Such precursors are converted to the fluorescent IO/IQ dye upon response to an external stimulus. The external stimulus can be an enzyme, light, heat, etc.

Advantageous examples are given below:

Scheme I: Examples of IO dyes and IO precursors a) IO dyes:

| Dye | R1 | R2 | R3 | R4 | R5 | R6 | R7 | R8 | R9 | X |
|---|---|---|---|---|---|---|---|---|---|---|
| Aldol ™ 470 dye | H | H | H | H | H | H | H | H | R12 | O |
| Aldol ™ 470 nitrogen dye | H | H | H | H | H | H | H | H | R12 | N |
| Aldol ™ 495 dye | H | H | Cl | H | H | H | H | H | R13 | O |
| Aldol ™ 515 dye | H | H | H | H | H | H | H | H | R14 | O |
| Aldol ™ 518 dye | H | H | Cl | H | H | H | H | H | R14 | O | wherein

Scheme I: Examples of IO dyes and IO precursors b) IO precursors:

| Precursor | LG | R1 to R9, X |
|---|---|---|
| Aldol ™ 470 beta-D-galactoside | beta-D-galactoside | See Aldol ™ 470 dye |
| Aldol ™ 470 L-alanine amide | L-alanine | See Aldol ™ 470 nitrogen dye |
| Aldol ™ 470 phosphate | phosphate | See Aldol ™ 470 dye |
| Aldol ™ 495 beta-D-galactoside | beta-D-galactoside | See Aldol ™ 495 dye |
| Aldol ™ 495 inositol-phosphate | inositol-phosphate | See Aldol ™ 495 dye |
| Aldol ™ 495 nonanoate | nonanoate | See Aldol ™ 495 dye |
| Aldol ™ 495 phosphate | phosphate | See Aldol ™ 495 dye |
| Aldol ™ 515 palmitate | palmitate | See Aldol ™ 515 dye |
| Aldol ™ 515 phosphate | phosphate | See Aldol ™ 515 dye |
| Aldol ™ 518 beta-D-galactoside | beta-D-galactoside | See Aldol ™ 518 dye |

The indirect method cannot only be used as a method to add the dye to the host or matrix at a location or time point defined through the external stimulus but also as a method to detect said external stimulus. This can be used for example to separate the resulting signal from the reaction solution which might be turbid or quenching, thus disturbing excitation or emission of solution borne signal molecules.

Accordingly, as a further aspect of the invention there is provided a method of specifically detecting an external stimulus, comprising the step of monitoring for the formation of a dye system as defined above.

In addition, IO/IQ precursors of ester types proved to be more stable than currently used fluorogenic compounds such as coumarin or fluorescein esters.

Plastics are labeled with fluorescent dyes for various reasons such as decorative purposes, as markers for protection against counterfeiting, for tracing production lots, for marking microspheres in flow cytometry. Labeling can be performed by incorporation of the dye during the production of the plastic ware. Labeling can also be done after the production by immersing the plastic in solvent dissolved dye or by printing techniques.

According to another aspect of the invention, a dye system as defined above is used as an originality marker, i.e. to label an item or its packaging so as to mark it as an original and distinguish it from counterfeits or forgeries.

Some particularly preferred embodiments are defined in the dependent claims.

According to one embodiment, the labile group LG is selected from the group consisting of acetate, beta-D-galactoside, inositol-phosphate, phosphate, palmitate, butyrate, acetate, nonanoate and L-alanine.

According to a further embodiment, the external stimulus is provided by an enzyme.

According to one embodiment, the host is selected from a solvent, polypropylene, polyethylene, mineral oil, silicone oil, an emulsion comprising mineral oil, an emulsion comprising silicon oil, cellulose nitrate, cellulose acetate, mixed cellulose esters. However, according to another embodiment, the host is substantially formed by the precursor itself.

According to one embodiment, the transformation step is carried out in the host, whereas in another embodiment the transformation step is carried out in an external medium, such as a suitable buffer system. This is then followed by the step of contacting the medium with the host, which may be e.g. a plastic tube, well plate or foil, thereby transferring the compound of formula (Ia or Ib) thus formed into the host and thus forming the dye system.

BRIEF DESCRIPTION OF THE FIGURES

The above mentioned and other features and objects of this invention and the manner of achieving them will become more apparent and this invention itself will be better understood by reference to the following description of various embodiments of this invention taken in conjunction with the accompanying drawings, wherein.

DETAILED DESCRIPTION OF THE INVENTION

The basis for many different embodiments of this invention is the discovery that Indoloindole and Indoloquinoline dyes show a strong fluorescence in certain hosts or matrices. In this description various IO dyes are given as illustrative examples (Scheme I) but these examples shall not limit the invention in any way. It was discovered that IO/IQ dyes have a strong solvatochromic effect. When, for example, the 470-, 495- and 515-dyes were dissolved in a series of solvents, the fluorescence of the solution was higher the lower the polarity of the solvent was. Weak or no fluorescence was detected in water, whereas a very strong fluorescence was seen in dichloromethane and oils (Table 1). It was also discovered that the fluorescence color might change with the solvent used. Interestingly, the fluorescence in acetone was higher than would have been expected from its dielectric constant.

TABLE 1

Fluorescence of IO dyes in various hosts

| Dye | Fluorescence | Water | Ethanol | Acetone | Dichloro-chloro-methane | Silicon oil | Mineral oil | Paraffin oil |
|---|---|---|---|---|---|---|---|---|
| 470 | intensity | Very weak | Very weak | Strong | Very strong | Weak | Medium | Medium |
|  | color | yellowish | orange | Green | Yellow-green | Yellow-green | Green | Green |
| 495 | intensity | None | Very weak | Strong | Very strong | Medium | Very strong | Very strong |
|  | color | None | Yellowish | Yellow-green | Yellow-green | Yellow-green | Green | Green |
| 515 | intensity | Very weak | Weak | Medium | Very strong | Very strong | Very strong | Very strong |
|  | color | Red | Red | Red | Red to yellow | Red | Yellow | Yellow-green |

Even more unexpectedly, it was found that some IO/IQ dyes go into and stain some hosts like polypropylene, polyethylene and similar plastics surprisingly easily and show a strong fluorescence in or on these hosts. Therefore, in one embodiment of the invention solutions or suspensions containing the IO/IQ dye (direct labeling) or the IO/IQ precursor (indirect labeling) are brought into contact with a suitable plastic. The dye (in case of the indirect labeling after applying a suitable stimulus) brings then fluorescence to the plastic. A direct labeling is possible by application of the IO/IQ dye. However, using the IO/IQ precursor as an in situ activatable precursor (similar to the principle of vat dyes) constitutes a further special way of applying the IO/IQ dye. This has several advantages. The solubility of the dye and the precursor can be different, thus making it possible to bring a soluble precursor to a desired location, where the insoluble dye is produced and precipitates at that location. Also, it allows the labeling to be dependent on a defined trigger, the labeling can be in a very confined area (e.g. laser activation of a photo labile indicator) and the indicator can be released in situ in a very finely dispersed consistency. The IO/IQ precursor can be activated by external stimuli that result in the conversion of the IO/IQ precursor to the IO/IQ dye. These external stimuli include but are not limited to: heating or temperature variations; electromagnetic irradiation; applied electric potentials; particular chemical environments such as acidic, alkaline, oxidizing or reducing; presence of particular chemical species such as ions, enzymes, oxygen or oxidizing agents, hydrogen or reducing agents; presence of particular biological species such as viruses, bacteria, fungi, antibodies, cells and cellular organelles, cellular tissue; and even plants, animals and humans as well as organs, bodily fluids, waste or decay thereof.

The fluorescence in the plastic is then used as e.g. an originality marker or as an indication of the activity of the external stimulus. The plastic might be present from the beginning and during the formation of the IO/IQ dye or added at the end after the dye has been generated from the precursor. In a preferred embodiment the plastic is a plastic vessel in which the reaction takes place.

When Aldol™ 495 beta-D-galactoside was incubated with beta-galactosidase in polypropylene tubes, a reddish color under white light and a green fluorescence under a standard UV 366 nm light was detected for the tubes containing beta-galactosidase but not for the tubes without beta-galactosidase. When the content of the tube was transferred to a new tube, immediately after transfer the new tube showed the same reddish color but practically no fluorescence (the fluorescence of the new tube increased with time after the transfer to the new tube). However, the emptied tube still had a strong green fluorescence, which also lasted after the tube was washed. Thus, the reddish color constitutes precipitated dye in the aqueous phase, but the fluorescence is located in or on the plastic and cannot be easily washed off. Besides the strong green fluorescent the tube showed a weak yellow-green color. The Aldol™ 495 beta-D-galactoside was also tested with *Escherichia coli* and *Salmonella enteritidis* in broth cultures. Cultures were incubated over night (16 h) and checked for fluorescence. As expected from the enzyme assays, tubes containing *E. coli* cultures were green fluorescent, tubes containing *S. enteritidis* not. The tubes were autoclaved with content, emptied and washed in a standard laboratory dishwasher. Autoclaving and washing did not change the fluorescence of the tubes (Table 3), demonstrating that the dye as well as the Aldol™ 495 beta-D-galactoside is stable under autoclaving conditions in the medium tested.

Figure 1:
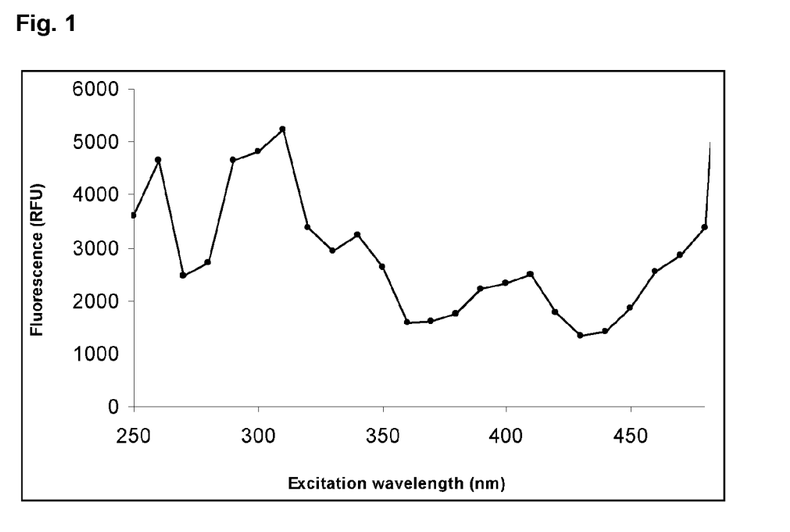
FIG. 1 shows the excitation spectrum of Aldol™ 495 dye in polypropylene ($\lambda_{em}$=510 nm)

The excitation and emission spectra of the Aldol™ 495 dye in PP were measured in a standard plate reader using a polypropylene microtiter plate that has been incubated with broth containing Aldol™ 495 beta-D-galactoside and an *E. coli* culture. The emission maximum was found to be at 510 nm. The optimal excitation is at 310 nm (FIG. 1). However, as shown above, also at 366 nm the excitation is sufficient to evoke a strong fluorescence, visible by the naked eye.

Figure 2:
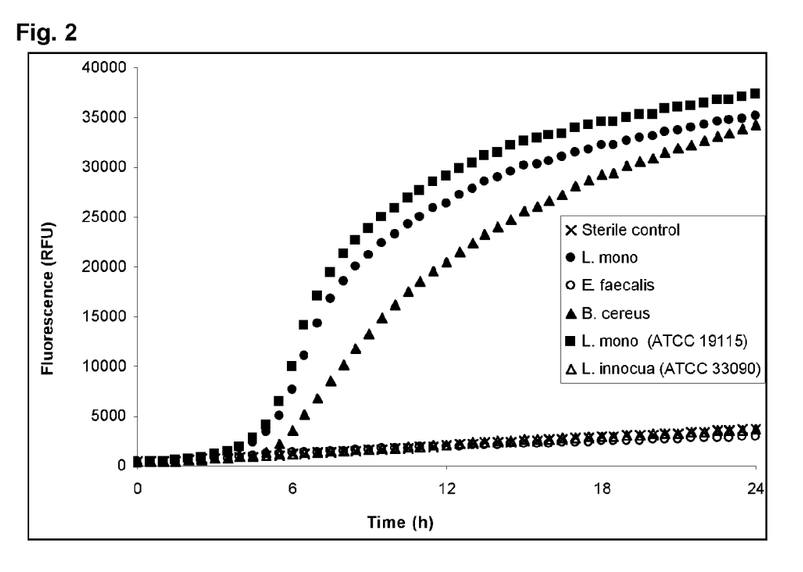
FIG. 2 shows the time course of fluorescence of cultures of Listeria monocytogenes, Bacillus cereus, Enterococcus faecalis, Listeria innocua, and sterile control in a medium containing Aldol™ 495 inositol-phosphate; cultures were grown in polypropylene microtiter plates at 37° C. in a Spectramax M5 platereader ($\lambda_{ex}$=310 nm, $\lambda_{em}$=510 nm); Fluorescence in arbitrary units (RFU, relative fluorescence units) is given vs. time (h)

In a preferred embodiment enzyme activity is monitored directly in multiwell plates with a fluorometer. Enzyme solutions, extracts or cells are added to wells of microtiter plates containing buffer or media. The microtiter plates have to be made from a suitable material (e.g. polypropylene but not polystyrene for the detection of the Aldol™ 495 dye). The enzymatic activity of the samples can then be followed with fluorescence measurements of microtiter plates. Such a scheme was tested with an indicator for phospholipase C. *Listeria* enrichment broth supplemented with Aldol™ 495 inositol-phosphate was inoculated with phospholipase C positive and phospholipase C negative strains. Fluorescence was detected in wells for positive strains (*Listeria monocytogenes, Bacillus cereus*), but not for negative strains (*Listeria innocua, Enterococcus faecalis*). Therefore, Aldol™ 495 inositol-phosphate is well suited for a continuous fluorescent assay for phospholipase C activity (FIG. 2).

As a further example the release of Aldol™ 470-, 495-, and 515 dyes from various Aldol™ acetate precursors through heat is given: The compounds were incubated at room temperature and at 90° C. for 40 min in PP tubes containing PE pellets. For comparison the more stable Aldol™ beta-D-galactoside precursors were treated the same way. Whereas for all tubes at room temperature neither coloration nor fluorescence was detected, the Aldol™ acetates but not the Aldol™ galactosides were instable at 90° C. and led to fluorescence of the PP and PE host (Table 2).

TABLE 2

Color and fluorescence of PP tubes and PE pellets (emptied and flushed with water) after heating for 40 min at 90° C.

| IO precursor | Color of tube | Fluorescence of tube |
|---|---|---|
| Aldol ™ 470 acetate | Light yellow | Medium blue-green fluorescence |
| Aldol ™ 495 acetate | Very light green | Strong green fluorescence |
| Aldol ™ 515 acetate | Very light orange | Medium yellow-green fluorescence |
| Aldol ™ 470 galactoside | No color | No fluorescence |
| Aldol ™ 495 galactoside | No color | No fluorescence |
| Aldol ™ 518 galactoside | No color | No fluorescence |

Figure 3:
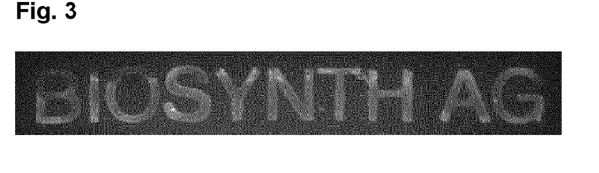
FIG. 3 shows a LDPE foil stamped with Aldol™ 515 dye; the imprint shows green fluorescence under UV 366 nm light.

In another embodiment the IO/IQ dye is directly applied to the plastic. This might be done by adding IO/IQ dye to the plastic during melting and molding or on the finished plastic product. On the finished product the dye might be applied in an aqueous suspension or a solvent solution. For example, Aldol™ 515 dye was dissolved in ethanol and applied to an ink pad. A stamp was first pressed on the ink pad then on a low density polyethylene (LDPE) foil. The pattern of the stamp was reproduced on the LDPE foil, made visible under UV 366 nm light (FIG. 3).

The application of dye to plastic can be improved by increasing the temperature. Aqueous suspensions of Aldol™ 470, 495, 515 and 518 dyes in PP tubes containing PE pellets were incubated at three different temperatures (22° C., 37° C., and 90° C.). The resulting fluorescence of PP tubes and PE pellets was much stronger after incubation at 90° C. for 5 hours than after 24 hours incubation at 37° C. or 22° C. Incubation at 37° C. led to more fluorescence than incubation at 22° C. Fluorescence after incubation at 22° C. was very weak, except for PE pellets incubated in the presence of Aldol™ 495 dye and Aldol™ 515 dye. It was observed that generally Aldol™ 495 dye led to more fluorescence than Aldol™ 515 dye, which led to more fluorescence than Aldol™ 518 dye and Aldol™ 470 dye. PE pellets showed more fluorescence than PP tubes.

Further embodiments take advantage of the fluorescence in oil. Aqueous solutions or suspensions containing the IO/IQ dye or the IO/IQ precursor are overlaid with oil in order to detect the IO/IQ dye by determining the fluorescence of the oil phase. Alternatively to an oil overlay also an oil emulsion can be used. The IO/IQ precursor in the aqueous phase can be generally any type of precursor, for example an enzyme labile, heat labile or photo labile indicator. In the case of enzyme indicators the enzymatic activity may originate from any kind of source e.g. from an extracted enzyme, from lysed or intact cells (prokaryotic or eukaryotic cells). The fluorescence measured in the oil phase is then used as an indication of enzyme activity. The oil might be present from the beginning and during the formation of the IO/IQ dye or only added at the end after the dye has been generated from the precursor.

Fluorescence development was tested with live cultures of E. coli and S. enteritidis in nutrient broth containing Aldol™ 518 beta-D-galactoside with or without paraffin oil overlay. No fluorescence was detected in cultures without oil overlay. However, tubes with oil showed a strong yellow-green fluorescence after incubation with E. coli but not after incubation with S. enteritidis. To test whether it was possible to evoke the fluorescence also after the incubation, oil was added to the cultures that have been incubated without oil. The tube containing the E. coli culture, but not the tube containing the S. enteritidis culture started to fluoresce after addition of oil. It took about 30 to 60 minutes until the E. coli culture overlaid with oil after incubation reached fluorescence values similar to the E. coli culture that had oil overlay from the beginning of the cultivation.

In a further embodiment fluorescence can be brought about in standard agar plates and nutrient broth by creating oil in water emulsions in these growth media. In one example, agar plates with Aldol™ 495 beta-D-galactoside in an emulsion of paraffin oil, Tween 80 and lecithin (1,2-dipalmitoyl-rac-glycero-3-phosphocholine) in standard nutrient agar were prepared. E. coli colonies grown on these plates were green fluorescent when observed under UV light after overnight incubation (16 h). Colonies grown under in plain Nutrient Agar with the Aldol™ 495 beta-D-galactoside alone did not show any fluorescence.

In another embodiment, the precursor itself can be used to create an emulsion, in which the dye produced from the precursor will fluoresce. In the absence of detergents, hydrophobic precursors such as e.g. Aldol™ 495 nonanoate and Aldol™ 515 palmitate do not go into solution in aqueous media, but exist as emulsions. When, for example, Salmonella are grown in a medium containing Aldol™ 495 nonanoate, they produce a yellow green fluorescence even in glass tubes. As shown above, galactosidase positive cultures with Aldol™ 495 beta-D-galactoside did not fluoresce in glass tubes, but only in polypropylene tubes. In the case of the 495 nonanoate, we assume that the dye produced from the Aldol™ 495 nonanoate by the C9 esterase activity of Salmonella gets dissolved in the emulsion of the Aldol™ 495 nonanoate and therefore becomes fluorescent. A finer emulsion and a stronger fluorescence signal were achieved when the Aldol™ 495 nonanoate indicator was added to the medium from a 20 mM stock solution than from a 200 mM stock solution (Table 7).

In another example Aldol™ 515 palmitate was used to mediate fluorescence of E. coli colonies on nutrient agar containing Aldol™ 518 beta-D-galactoside as well as Aldol™ 515 palmitate. The Aldol™ 518 dye produced by the E. coli beta-galactosidase from Aldol™ 518 beta-D-galactoside will fluoresce due to the presence of Aldol™ 515 palmitate.

These illustrations show that suitable additives added to the medium can induce or increase the fluorescence of the IO/IQ dye. The additives mentioned are only some examples; other additives with similar properties can be selected by those of skill in the art.

Membrane filtration is a widely used technique to detect and quantify microbial contamination. It was discovered that due to the matrix effect of the membrane filter, fluorescence of various IO/IQ dyes was considerably stronger in colonies grown on standard membrane filters than on nutrient agar plates without filter (Table 5). Therefore, IO/IQ indicators are suited for use as fluorescent markers for increased sensitivity in membrane filter applications.

Western Blotting is a routine technique for protein analysis. A widely used, cost-effective and simple way for signal detection is the reaction of a chromogenic phosphatase indicator with alkaline phosphatase coupled to the secondary antibody, yielding a colored band or spot. The IO/IQ indicators offer an easy way for fluorescent and chromogenic western blotting based on the same principle as the common chromogenic western blotting, the only difference being the phosphatase indicator. When in a standard dot blot protocol on nitrocellulose membrane the chromogenic BCIP/NBT was replaced with Aldol™ 470 phosphate, yellow-green fluorescent dots appeared under UV light within minutes after start of the development reaction. In addition, after longer incubation the dots were also clearly identified under white light through their yellow color. Thus, IO/IQ indicators offer a way of performing chromogenic and fluorogenic blotting assay at the same time.

EXAMPLES

Example 1

Enzyme Assay 100 mM sodium phosphate buffer (pH 7.3) containing 1 mM $MgCl_2$ and 0.5 mM Aldol™ 495 beta-D-galactoside, was distributed into glass, polystyrene and polypropylene tubes (two of each). Purified E. coli beta-galactosidase was added to half of the tubes, the other half serving as negative controls. Color under white light and fluorescence was monitored under UV 366 nm. In all three tubes with beta-galactosidase enzyme, but in none of the negative controls, a red-brown precipitate was observed. A green fluorescence was only detected in the polypropylene tube with beta-galactosidase, but neither in the glass nor polystyrene tubes nor in the polypropylene tube without enzyme. The content of the fluorescent polypropylene tube was then transferred into a new polypropylene tube. The emptied polypropylene tube still showed the same intensity of green fluorescence as before the transfer. The new tube did not show fluorescence just after the transfer, but started to fluoresce after around 10 minutes.

Example 2

Peptone Broth with E. coli, S. enteritidis

Peptone broth (20 g/l peptone, 5 g/l NaCl, pH 7.4) containing 0.4 mM Aldol™ 495 beta-D-galactoside was dispensed into polypropylene and glass test tubes. The tubes were inoculated with E. coli and S. enteritidis, respectively, and incubated at 37° C. for 7 days. In the end, tubes were autoclaved, emptied and washed in a dishwasher. Fluorescence of tubes was checked at different time points. Whereas no fluorescence was detected in any of the glass tubes, the Aldol™ 495 beta-D-galactoside indicator proved suitable to differentiate between E. coli and S. enteritidis by fluorescence in polypropylene tubes (Table 3).

TABLE 3

Aldol ™ 495 beta-D-galactoside in peptone broth

| | Fluorescence of PP tube under UV light (366 nm) | |
|---|---|---|
| Time point | E. coli | S. enteritidis |
| 16 h incubation | Strong green | No fluorescence |
| After autoclaving and emptying tube | Strong green | No fluorescence |
| After washing in dish-washer | Strong green | No fluorescence |

Example 3

Stamping on LDPE

Three pieces of felt were soaked with ethanol containing 0.5 mM of Aldol™ 470, Aldol™ 495 or Aldol™ 515 dye respectively. A stamp was pressed first on the felt then on a piece of low density polyethylene film. The film was left to dry for 15 minutes and then exposed to various treatments (Table 4). The stamping with the Aldol™ 515 dye proved most stable under the conditions tested.

TABLE 4

IO dyes printed on LDPE film.

| Treatment | Aldol ™ 470 dye | Aldol ™ 495 dye | Aldol ™ 515 dye |
|---|---|---|---|
| 15 min after stamping | Medium blue-green fluorescence | Strong green fluorescence | Strong yellow-green fluorescence |
| After short flushing with ethanol | Medium blue-green fluorescence | Strong green fluorescence | Strong yellow-green fluorescence |
| After soaking for 18 h in water | Medium blue-green fluorescence | Medium green fluorescence | Strong yellow-green fluorescence |
| After soaking for 18 h in ethanol | No fluorescence | No fluorescence | No fluorescence |
| After 70 h exposure to white neon light | Weak blue-green fluorescence | Very weak green fluorescence | Strong yellow-green fluorescence |

Example 4

Fluorescence on Membrane Filters

Nutrient agar (5 g/l peptone, 5 g/l NaCl, 2 g/l yeast extract, 1 g/l beef extract, 13 g/l agar, pH 7.4) was autoclaved and cooled to 50° C. Plates were poured containing 0.4 mM of Aldol™ 470 beta-D-galactoside, Aldol™ 495 beta-D-galactoside, Aldol™ 518 beta-D-galactoside, or Aldol™ 470 L-alanine amide, respectively. The indicators were added to the agar from 50 mM stock solutions in DMF just before pouring the plates.

Sterile membrane filters were placed at the surface of the gelled agar plates. 10 µl of diluted E. coli culture were added to the filter, let dry and incubated at 37° C. Fluorescence of single colonies after 14-16 hours of incubation was stronger on filters than on naked agar (Table 5).

TABLE 5

Fluorescence of E. coli colonies after 14-16 hours incubation at 37° C. on different hosts.

| | Naked nutrient agar | Cellulose nitrate | Cellulose acetate |
|---|---|---|---|
| Aldol ™ 470 beta-D-galactoside | Weak orange fluorescence | Medium green fluorescence | Medium green fluorescence (stronger than on cellulose nitrate) |
| Aldol ™ 495 beta-D-galactoside | No fluorescence | Medium to strong yellow fluorescence | Medium to strong green fluorescence |
| Aldol ™ 518 beta-D-galactoside | Weak red fluorescence | Strong red fluorescence | Strong red fluorescence |
| Aldol ™ 470 L-alanine amide | No fluorescence | Very weak green fluorescence | Medium blue-green fluorescence |

Example 5

Cultures with Oil Overlay

Test tubes with 3 ml Nutrient Broth (5 g/l peptone, 5 g/l NaCl, 2 g/l yeast extract, 1 g/l beef extract, pH 7.4) containing 0.4 mM Aldol™ 518 beta-D-galactoside (added to the autoclaved cooled medium from a stock solution of 50 mM in DMF) and overlaid with either 0, 50 or 300 µl paraffin oil were inoculated either with E. coli, S. enteritidis or with sterile water. After 16, 21, 48 hours of incubation at 37° C., pictures were taken under white light and UV 366 nm illumination (Table 6). The tube with E. coli showed a red coloration of the medium, no fluorescence in the medium was detected. However, in the tubes with oil the oil overlay showed a strong yellow-green fluorescence. In the tube with S. enteritidis, the color of the medium was beige and no fluorescence, neither in the medium nor in the oil phase was seen.

After 40 h of incubation 50 µl oil was added to the tube without oil. After 30-60 min the fluorescence of the oil overlay was similar to the one in the tube with oil from the beginning.

TABLE 6

Color and fluorescence of broth containing Aldol ™ 518 beta-D-galactoside

| | | E. coli | | | S. enteritidis | | |
|---|---|---|---|---|---|---|---|
| Paraffin oil overlay | | 16 h | 21 h | 40 h | 16 h | 21 h | 40 h |
| 0 µl | Growth | + | + | + | + | + | + |
| | Color | Red | Red | Red | Beige | Beige | Beige |
| | Fluorescence (yellow-green) | − | − | − | − | − | − |
| 50 µl | Growth | + | + | + | + | + | + |
| | Color | Red | Red | Red | Beige | Beige | Beige |
| | Fluorescence (yellow-green) | + | ++ | +++ | − | − | − |
| 300 µl | Growth | + | + | + | + | + | + |
| | Color | Red | Red | Red | Beige | Beige | Beige |
| | Fluorescence (yellow-green) | ++ | +++ | +++ | − | − | − |

Example 6

Listeria Assay in Polypropylene Microtiter Plates

Figure 4:
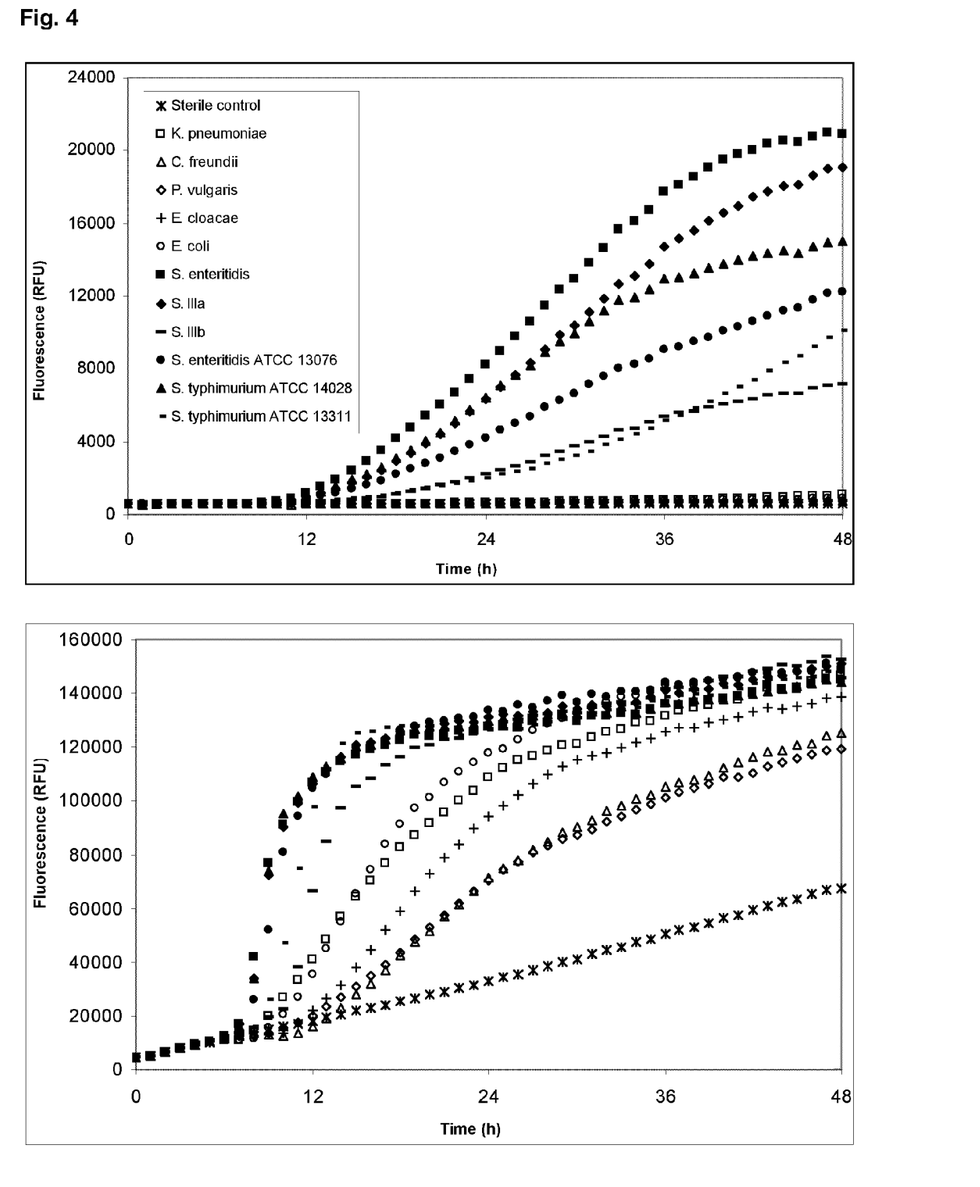
FIG. 4 shows the time course of fluorescence of cultures of Klebsiella pneumoniae, Citrobacter freundii, Proteus vulgaris, Enterobacter cloacae, Escherichia coli, Salmonella enteritidis (2 strains), Salmonella typhimurium (2 strains) Salmonella IIIa, Salmonella IIIb and sterile control in a medium containing Aldol™ 495 nonanoate (top graph) or 4-Methylumbelliferyl nonanoate (bottom graph); cultures were grown in polystyrene microtiter plates at 37° C. in a Spectramax M5 platereader ($\lambda_{ex}$=360 nm, $\lambda_{em}$=560 nm (top graph) and 460 nm (bottom graph)); fluorescence in arbitrary units (RFU, relative fluorescence units) is given vs. time (h).

M52 Listeria enrichment broth (see FDA's Bacteriological Analytical Manual) without the 3 selective agents was prepared with (3.2 g/l) and without bovine serum albumin (BSA) and supplemented with 0.4 mM Aldol™ 495 inositol-phosphate. This medium was inoculated with *L. monocytogenes* (2 strains), *L. innocua*, *B. cereus* and *E. faecalis* and incubated at 37° C. in microtiter plates made of polypropylene in a platereader for 24 hours. Fluorescence (excitation at 310, 360, and 410 nm, emission at 510 nm) was recorded every 30 min. A strong increase in fluorescence was observed for *L. monocytogenes* and *B. cereus* strains, which are known to be positive for phospholipase C. The phospholipase C negative strains *L. inoccua* and *E. faecalis* showed only a very slow increase of fluorescence similar to the sterile control (FIG. 4). All tested strains grew in the medium as indicated by the turbidity of the medium. The fluorescence increase in the medium with BSA was faster than in the medium without BSA. Aldol™ 495 inositol-phosphate is well suited for a continuous fluorescent assay for phospholipase C activity.

Example 7

Dot Blot 0.16 μg of beta-galactosidase in 4 μl of phosphate buffer was spotted on a nitrocellulose membrane. The membrane was dried for 15 min and then blocked in TBS-T (20 mM Tris-HCl, 150 mM NaCl, 0.05% Tween20, pH 7.5) with 5% BSA for one hour. Then the membrane was incubated with a rabbit anti-beta-galactosidase antibody in TBS-T/5% BSA for one hour, washed three times for 5 min in TBS-T, and incubated with a phosphatase coupled goat anti rabbit antibody in TBS-T/5% BSA for one hour. The membrane was washed again three times for 5 min in TBS-T and twice with assay buffer (20 mM Tris-HCl (pH 9.5) and 1 mM $MgCl_2$) for 2 min and finally incubated with 0.4 mM Aldol™ 470 phosphate in assay buffer. After a few minutes of incubation the spot containing the beta-galactosidase started to show yellow fluorescence under UV 366 nm light. With longer incubation, after about 20 min the spot showed also a yellow coloration under ambient light. No fluorescence or coloration was observed for a spot of alpha-amylase (negative control).

Example 8

Nutrient Agar with Oil in Water Emulsion

Nutrient agar (5 g/l peptone, 5 g/l NaCl, 2 g/l yeast extract, 1 g/l beef extract, 13 g/l agar, pH 7.4) containing 1.25% paraffin oil, 0.15% 1,2-dipalmitoyl-rac-glycero-3-phosphocholine, 0.1% Tween 80 and 0.4 mM Aldol™ 495 beta-D-galactoside was vortexed well, autoclaved, cooled to 50° C. and vortexed well again before pouring plates. For comparison Nutrient agar plates with 0.4 mM Aldol™ 495 beta-D-galactoside but without further additions were prepared. Solidified plates were inoculated with an *E. coli* culture and incubated over night at 37° C. Plates were inspected under UV 366 nm light after 16 hours of incubation. On the plates containing in addition to the Aldol™ 495 beta-D-galactoside also oil, Tween 80 and 1,2-dipalmitoyl-rac-glycero-3-phosphocholine the *E. coli* colonies were green fluorescent. On the plates containing only the Aldol™ 495 beta-D-galactoside the colonies did not show any fluorescence.

Example 9

Fluorescence of Aldol™ 495 Nonanoate

Autoclaved Nutrient broth was supplemented with 0.4 mM Aldol™ 495 nonanoate from a stock solution of either 50 mM or 200 mM in DMF or DMSO. This broth was inoculated with either *E. coli*, *S. enteritidis* or sterile water and was pipetted to wells of a polystyrene microtiterplate. The plate was incubated in a plate reader at 37° C. and fluorescence was measured periodically (excitation at 360 nm, emission at 560 nm). Fluorescence values (relative fluorescence units=RFU) for various time points are given in Table 7. For the *S. enteritidis* culture RFU increased strongly within the first 48 hours of incubation and then decreased between 48 h and 120 h. The later decrease is probably a cause of the lower concentration of Aldol™ 495 nonanoate due to degradation by *S. enteritidis*. For the *E. coli* culture RFU were practically constant during the first 18 hours and then started to increase slowly between 18 h and 120 h. The later increase can be caused either by a low esterase activity of *E. coli* or by an increased hydrolysis due to the alkalinization of the media after growth of *E. coli*. The RFU of the sterile control only increased slightly during 120 h of incubation.

TABLE 7

Fluorescence values (RFU) of cultures containing Aldol ™ 495 nonanoate (glass tubes).

| Species | Concentration of stock solution (mM) | 0 h | 12 h | 18 h | 48 h | 120 h |
|---|---|---|---|---|---|---|
| Sterile control | 50 | 392 | 445 | 434 | 511 | 523 |
| E. coli | 50 | 424 | 463 | 551 | 1710 | 3851 |
| S. enteritidis | 50 | 406 | 2922 | 10047 | 45027 | 13424 |
| Sterile control | 200 | 433 | 399 | 411 | 422 | 455 |
| E. coli | 200 | 444 | 404 | 468 | 774 | 1924 |
| S. enteritidis | 200 | 412 | 1812 | 3449 | 8403 | 5169 |

Example 10

Aldol™ 495 Nonanoate and 4-Methylumbelliferone Nonanoate in Buffered Peptone Water in Polystyrene Plates Buffered peptone water containing either 0.4 mM Aldol™ 495 nonanoate or 0.2 mM 4-methylumbelliferyl nonanoate was dispensed in a microtiter plate and inoculated with about 700 cfu/ml of various bacterial strains. The cultures were incubated in a plate reader at 37° C. and fluorescence measured every hour for 48 hours. An excitation wavelength of 360 nm was used for both dyes, the emission wavelength was 560 nm for the Aldol™ 495 dye and 460 nm for the 4-methylumbelliferone. Whereas strong fluorescence was detected for C9 esterase negative strains and even the sterile control within 12-24 hours in broth containing 4-methylumbelliferyl nonanoate, the fluorescence was specific for *Salmonella* strains in the broth with Aldol™ 495 nonanoate (FIG. 4). This shows that the Aldol™ indicator is less prone to unspecific hydrolysis than the 4-methylumbelliferone indicator.

Example 11

Anaerobic Incubation for Detection of *Clostridia perfringens* by Membrane Filtration Schaedler Agar (Oxoid) was autoclaved and cooled to 50° C. Plates were poured containing Aldol™ 470 phosphate, Aldol™ 495 phosphate, or Aldol™ 515 phosphate, respectively. The indicators were added to the agar from 50 mM stock solutions in DMF just before pouring the plates at concentrations of 0.2, 0.1, and 0.05 mM.

Water spiked with *Clostridia perfringens* cells was filtered through cellulose acetate membrane filters. After filtration the filters were placed at 6. The dye system according to claim 4, wherein said host is selected from a solvent with a room-temperature dielectric constant ∈≤10.0, polypropylene, polyethylene, mineral oil, silicone oil, an emulsion comprising mineral oil, an emulsion comprising silicone oil, cellulose nitrate, cellulose acetate, mixed cellulose esters.

7. A method of producing a dye system according to claim 4, comprising the step of providing a precursor compound having the general formula (IIa):

(IIa)

or (IIb):

(IIb)

wherein
R1, R2, R3, R4, R5, R6, R7, R8, R9, R10 and R11 are selected from the group consisting of hydrogen; C1-4 alkyl; C1-4 alkoxy; fused or linearly connected aryl; fused or linearly connected heteroaryl; halogen; cyano; nitro; formyl and optionally substituted amino, carboxy, carbonyl, hydroxy and sulphonyl;
X is selected from O, NH or S;
LG is a labile group with the X-LG moiety being susceptible to conversion by action of an external stimulus; and
Z is selected from O, NH or S;
followed by the step of subjecting said precursor compound to said external stimulus so as to transform said compound of formula (IIa or IIb) to a corresponding compound of formula (Ia or Ib).

8. The method according to claim 7, wherein said external stimulus is provided by an enzyme.

9. The method according to claim 7, wherein said labile group LG is selected from the group consisting of acetate, beta-D-galactoside, inositol-phosphate, phosphate, palmitate, butyrate, acetate, nonanoate and L-alanine.

10. The method according to claim 7, wherein said host consists of said precursor.

11. The method according to claim 7, wherein said transformation step is carried out in said host.

12. The method according to claim 7, wherein said transformation step is carried out in a medium outside of said host, followed by contacting said medium with said host, thereby transferring the compound of formula (Ia or Ib) thus formed into said host, so as to form said dye system.

13. A method of specifically detecting an external stimulus, comprising the step of monitoring for the formation of a dye system according to claim 7.

14. The method of using a dye system according to claim 4 comprising the step of applying the dye system on an item or its packaging as an originality marker.

15. The method according to claim 2, wherein said host is selected from the group consisting of:
a solvent with a room temperature dielectric constant ∈≤10.0,
polypropylene,
polyethylene,
mineral oil,
silicone oil,
an emulsion comprising mineral oil,
an emulsion comprising silicone oil,
cellulose nitrate,
cellulose acetate, and
mixed cellulose esters.

16. The dye system according to claim 5, wherein said host is selected from a solvent with a room-temperature dielectric constant ∈≤10.0, polypropylene, polyethylene, mineral oil, silicone oil, an emulsion comprising mineral oil, an emulsion comprising silicone oil, cellulose nitrate, cellulose acetate, mixed cellulose esters.

17. A method of producing a dye system according to claim 5, comprising the step of providing a precursor compound having the general formula (IIa):

(IIa)

or (IIb):

(IIb)

wherein
R1, R2, R3, R4, R5, R6, R7, R8, and R11 are selected from the group consisting of hydrogen; C1-4 alkyl C1-4 alkoxy; fused or linearly connected aryl; fused or linearly connected heteroaryl; halogen; cyano; nitro; formyl and optionally substituted amino, carboxy, carbonyl, hydroxy and sulphonyl;
R9 is selected from one of the following:

X is selected from O, NH or S;
LG is a labile group with the X-LG moiety being susceptible to conversion by action of an external stimulus; and
Z is selected from O, NH or S;
followed by the step of subjecting said precursor compound to said external stimulus so as to transform said compound of formula (IIa or IIb) to a corresponding compound of formula (Ia or Ib).

18. A method of producing a dye system according to claim comprising the step of providing a precursor compound having the general formula (IIa):

or (IIb)

wherein
R1, R2, R3, R4, R5, R6, R7, R8, R9, R10 and R11 are selected from the group consisting of hydrogen; C1-4 alkyl; C1-4 alkoxy; fused or linearly connected aryl; fused or linearly connected heteroaryl; halogen; cyano; nitro; formyl and optionally substituted amino, carboxy, carbonyl, hydroxy and sulphonyl;
X is selected from O, NH or S;
LG is a labile group with the X-LG moiety being susceptible to conversion by action of an external stimulus; and
Z is selected from O, NH or S;
followed by the step of subjecting said precursor compound to said external stimulus so as to transform said compound of formula (IIa or IIb) to a corresponding compound of formula (Ia or Ib).

19. The method according to claim 8, wherein said labile group LG is selected from the group consisting of acetate, beta-D-galactoside, inositol-phosphate, phosphate, palmitate, butyrate, acetate, nonanoate, and L-alanine.

20. The method according to claim 8, wherein said host consists of said precursor.

21. The method according to claim 9, wherein said host consists of said precursor.

22. The method according to claim 8, wherein said transformation step is carried out in said host.

23. The method according to claim 9, wherein said transformation step is carried out in said host.

24. The method according to claim 10, wherein said transformation step is carried out in said host.

25. The method according to claim 8, wherein said transformation step is carried out in a medium outside of said host, followed by contacting said medium with said host, thereby transferring the compound of formula (Ia or Ib) thus formed into said host, so as to form said dye system.

26. The method according to claim 9, wherein said transformation step is carried out in a medium outside of said host, followed by contacting said medium with said host, thereby transferring the compound of formula (Ia or Ib) thus formed into said host, so as to form said dye system.

27. A method of specifically detecting an external stimulus, comprising the step of monitoring for the formation of a dye system according to claim 8.

28. A method of specifically detecting an external stimulus, comprising the step of monitoring for the formation of a dye system according to claim 9.

29. A method of specifically detecting an external stimulus, comprising the step of monitoring for the formation of a dye system according to claim 10.

30. A method of specifically detecting an external stimulus, comprising the step of monitoring for the formation of a dye system according to claim 11.

31. A method of specifically detecting an external stimulus, comprising the step of monitoring for the formation of a dye system according to claim 12.

32. The method of using a dye system according to claim 5 comprising the step of applying the dye system on an item or its packaging as an originality marker.

33. The method of using a dye system according to claim 6 comprising the step of applying the dye system on an item or its packaging as an originality marker.

* * * * *

UNITED STATES PATENT AND TRADEMARK OFFICE
CERTIFICATE OF CORRECTION

PATENT NO.       : 9,157,917 B2  
APPLICATION NO.  : 13/883067  
DATED            : October 13, 2015  
INVENTOR(S)      : Wick et al.

Page 1 of 1

It is certified that error appears in the above-identified patent and that said Letters Patent is hereby corrected as shown below:

IN THE CLAIMS

Claim 17, column 21, line 2, insert --R10-- after "R8"

Claim 18, column 21, line 27, insert --6-- after "claim"

Signed and Sealed this
Eighth Day of December, 2015

Michelle K. Lee
*Director of the United States Patent and Trademark Office*